US010537693B2

(12) United States Patent
Dennis

(10) Patent No.: US 10,537,693 B2
(45) Date of Patent: Jan. 21, 2020

(54) COLLAPSIBLE DISPOSABLE SPACER FOR METERED DOSE INHALERS

(71) Applicant: MEDICAL DEVELOPMENTS INTERNATIONAL LIMITED, Scoresby, Victoria (AU)

(72) Inventor: John Dennis, Calgary (CA)

( * ) Notice: Subject to any disclaimer, the term of this patent is extended or adjusted under 35 U.S.C. 154(b) by 0 days.

(21) Appl. No.: 16/305,942

(22) PCT Filed: May 29, 2017

(86) PCT No.: PCT/AU2017/050501
§ 371 (c)(1),
(2) Date: Nov. 30, 2018

(87) PCT Pub. No.: WO2017/205907
PCT Pub. Date: Dec. 7, 2017

(65) Prior Publication Data
US 2019/0151578 A1 May 23, 2019

(30) Foreign Application Priority Data
May 30, 2016 (AU) .............................. 2016902049

(51) Int. Cl.
*A61M 15/00* (2006.01)
(52) U.S. Cl.
CPC ...... *A61M 15/0088* (2014.02); *A61M 15/009* (2013.01); *A61M 15/0021* (2014.02)
(58) Field of Classification Search
CPC .......... A61M 15/0086; A61M 15/0088; A61M 15/0021; A61M 15/0023; A61M 11/00;
(Continued)

(56) References Cited

U.S. PATENT DOCUMENTS 4,174,712 A 11/1979 Moren et al.
4,470,412 A 9/1984 Nowacki et al.
(Continued)

FOREIGN PATENT DOCUMENTS

WO 1996037249 A1 11/1996
WO 2008124666 A2 10/2008

OTHER PUBLICATIONS

International Search Report and Written Opinion for corresponding international application No. PCT/AU2017/050501 dated Jul. 12, 2017.

*Primary Examiner* — Michael J Tsai
(74) *Attorney, Agent, or Firm* — Westman, Champlin & Koehler, P.A.

(57) ABSTRACT

The present invention is a collapsible/expandable and disposable spacer for use with a metered dose inhaler ('MDI'). One embodiment of the invention is a spacer collapsible into a substantially flat configuration for storage and expandable into a spacer volume for use with a metered dose inhaler (MDI) wherein the spacer comprises: (a) a collapsible and expandable panel arrangement internally located within the spacer volume to divide the spacer volume into a MDI medicament delivery chamber and an inhalation/exhalation chamber when the spacer is in an expanded configuration; (b) a medicament delivery opening adapted to receive a MDI in a MDI medication delivery end of the MDI medicament delivery chamber; (c) an inhalation opening in a mouthpiece end of the inhalation/exhalation chamber; (d) an exhalation opening in the inhalation/exhalation chamber; and further wherein the panel arrangement comprises an aperture off-set from the medicament delivery opening with the proviso that the aperture is not a valved aperture.

17 Claims, 3 Drawing Sheets

(58) Field of Classification Search
CPC .. A61M 11/005; A61M 11/006; A61M 11/02; A61M 11/08
See application file for complete search history.

(56) References Cited

U.S. PATENT DOCUMENTS

| | | | | |
|---|---|---|---|---|
| 4,938,210 | A | * | 7/1990 | Shene ............... A61M 15/0086 128/200.23 |
| 4,953,545 | A | | 9/1990 | McCarty |
| 5,012,803 | A | | 5/1991 | Foley et al. |
| 5,318,016 | A | * | 6/1994 | Mecikalski ....... A61M 15/0086 128/200.14 |
| 5,385,140 | A | | 1/1995 | Smith |
| 5,427,089 | A | | 6/1995 | Kraemer |
| 5,571,246 | A | * | 11/1996 | Alldredge ......... A61M 15/0086 128/200.14 |
| 5,816,240 | A | | 10/1998 | Komesaroff |
| 6,202,643 | B1 | | 3/2001 | Sladek |
| 6,345,617 | B1 | | 2/2002 | Engelbreth et al. |
| 6,463,929 | B1 | * | 10/2002 | Scheuch ........... A61M 15/0086 128/200.22 |
| 6,550,473 | B1 | | 4/2003 | Sladek |
| 6,679,252 | B2 | | 1/2004 | Sladek |
| 7,107,987 | B2 | | 9/2006 | Sundaram et al. |
| 7,201,164 | B2 | | 4/2007 | Gruchowski et al. |
| 2002/0129814 | A1 | | 9/2002 | Sladek |
| 2003/0010336 | A1 | * | 1/2003 | Vito ................. A61M 15/0086 128/200.22 |
| 2009/0032019 | A1 | | 2/2009 | Green et al. |
| 2010/0163045 | A1 | * | 7/2010 | Powell .................. A61M 11/00 128/203.29 |

\* cited by examiner

COLLAPSIBLE DISPOSABLE SPACER FOR METERED DOSE INHALERS

CROSS-REFERENCE TO RELATED APPLICATION

This Application is a Section 371 National Stage Application of International Application No. PCT/AU2017/050501, filed May 29, 2017, and published as WO 2017/205907 on Dec. 7, 2017, in English, the contents of which are hereby incorporated by reference in their entirety.

FIELD

The present invention provides a collapsible/expandable and disposable spacer for use with a metered dose inhaler ('MDT').

BACKGROUND

Spacers (also known as, for example, chambers, dispersion chambers, valved chambers etc.) for use with MDI's are known. The benefits of using a spacer with an MDI to deliver medicaments may include assisting a patient to self-administer MDI medicaments. For example, a spacer may improve the delivery of the inhaled drugs to the patient's bronchial tubes and/or lungs by breaking up, slowing down and/or dispersing the discharged medication to enhance mist formation and reduce oropharyngeal deposition.

Spacers have traditionally been designed for re-use. They are therefore typically made from rigid polymeric materials or the like and require a user to ensure they are kept in good working condition which involves regular cleaning to avoid the accumulation of deposited medicaments and bacterial contamination. Some examples of reusable spacers are described in U.S. Pat. No. 4,174,712 (Moren et. al.), U.S. Pat. No. 4,470,412 (Nowacki et. al.), U.S. Pat. No. 5,012,803 (Foley et. al.), U.S. Pat. No. 5,385,140 (Smith), U.S. Pat. No. 5,427,089 (Kraemer) and U.S. Pat. No. 5,816,240 (Komesaroff).

While spacers are generally cylindrical in shape, other shapes have been described. For example, U.S. Pat. No. 7,107,987 (Sundaram et. al.) describes a spacer having a first conical body joined to a second conical body. When in use, the spacer is described as limiting deposition of the medicament by channelling the spray down its centreline which reduces contact between medication particles and the walls of the spacer. The spacer design is described as taking advantage of the high-pressure recirculation zones that tend to force the medication spray away from the walls of the spacer into a preferred, central spray pattern so that a high percentage of the medication is delivered deep into the lung regions of a patient. In one embodiment the spacer comprises a unidirectional valve provided proximate to the mouthpiece. In another embodiment the spacer comprises at least one conical body that is collapsible so that the spacer occupies less storage space when not in use.

Another type of spacer design is described in U.S. Pat. No. 7,201,164 (Grychowski et. al.). The spacer comprises a holding chamber which tapers to a narrow orifice from a medicament upstream end to a downstream end. Preferred embodiments comprise inhalation and exhalation valves. The narrow orifice alone or in conjunction with the tapered channel is described as maximising the emitted dose and respirable fraction of the aerosol, more specifically, increasing the velocity and the number of respirable particles and concentrating them along the axis or centreline of the channel. The spacer is said to be particularly suited to users (such as children or the elderly) with low tidal volumes.

U.S. Pat. No. 6,345,617 (Engelbreth et. al.) describes an aerosol medication delivery apparatus which comprises a canister-holding portion and a chamber housing. The chamber housing includes a containment baffle that partially blocks the output (i.e. mouthpiece) end. The containment baffle is described as having a concave surface facing the input end and functions to reduce the velocity or flow rate or both of the aerosol medication particles which are delivered from the pressurised MDI along the longitudinal axis (i.e. axis of symmetry) of the chamber housing. The aerosol medication particles that have a flow path away from the axis of symmetry tend to have a velocity that is lower than that of the particles near to the axis of symmetry. Further, it is described that upon discharge, the on-axis aerosol medication particles which are generally non-respirable and have a higher inertia than the respirable particles, collide with the interior centre portion of the containment baffle resulting in a reduction in the number of larger (non-respirable) aerosol medication particles into smaller respirable particles. In one embodiment the containment baffle is described as having four relatively large openings formed around the periphery of a solid dish-shaped central portion to provide a surface area that serves to prevent aerosol particles having a high velocity from passing to the patient.

Disposable spacers are known. For example, U.S. Pat. No. 4,953,545 (McCarty) describes a plastic disposable chamber which tapers, much like a take-away coffee cup, outwardly from the MDI input end towards the mouthpiece end.

Collapsible and/or expandable disposable spacers are also known. For example, U.S. Pat. No. 6,202,643 (Sladek) (see also related U.S. Pat. No. 6,550,473 (Sladek) and U.S. Pat. No. 6,679,252 (Sladek)) describes a collapsible, disposable valved chamber which may be constructed from a single punched sheet of suitable material such as paperboard, plastic, spun non-woven polymer such as TYVEK by DuPont or the like. A key feature of the invention is the one-way inhalation valve is described as being disposed between the mouthpiece opening and a first volume of the chamber to allow a one-way flow of gas from the first volume to the mouthpiece opening. The one-way inhalation valve is further described as including an inhalation flap (or membrane) and valve seat. Exhalation by a patient through the mouthpiece opening presses the inhalation flap against the valve seat to prevent the flow of exhaled gas from the mouthpiece opening back into the first volume, the exhaled gas flowing through an opening in the mouthpiece section between the one-way inhalation valve and the mouthpiece opening. Inhalation by a patient through the mouthpiece opening causes a portion of the inhalation flap to move away from the valve seat to provide a path for the flow of gas from the first volume into the mouthpiece section. In use, the patents describe that the relative vacuum created by the patient's inhaling causes the inhalation flap to pivot or swing away from the opening in the inhalation valve panel. This is to enable a substantial portion of the ejected plume of medication to pass through the inhalation valve opening and the mouthpiece end opening into the mouth of the patient. When the patient exhales before repeating the above procedure the inhalation flap is forced, by the increased pressure caused by the patient exhaling, against the peripheral portion of the inhalation panel around the inhalation opening. The exhaled air then flows through an exhalation opening as it pushes an exhale flap outward so that the exhaled air escapes to the outside atmosphere.

Related U.S. Pat. No. 6,679,252 (Sladek) describes a further embodiment of the construction and operation of the expandable/collapsible valved chamber from a single sheet (see for example FIGS. 19A-F). Notably described is the formation of a good seal to prevent both the inhaled and exhaled air from bypassing the inhalation valved chamber which is said to substantially increase the efficiency of the valved chamber. Referring to FIG. 19E, when the valved chamber is fully "popped-up" for use by a patient, the panel comprising the inhalation valve is in a nearly vertical position thereby providing a nearly vertical wall that separates the first volume between the inhalation valve assembly and the MDI boot adapter panel and a second volume between the inhalation valve assembly and the inhalation/exhalation openings.

A common feature of known spacers, including those described herein, is the tendency to comprise a valve or diaphragm arrangement to control the flow of air through the spacer as the patient inhales and/or exhales the medicament. The valves may typically be made from polymeric materials and when employed for reusable spacers, require regular cleaning to avoid the accumulation of deposited medicaments and bacterial contamination. In the case of, for example, the collapsible/expandable and disposable spacers described in U.S. Pat. Nos. 6,202,643, 6,550,473 and 6,679, 252 (above), the inhalation valve assembly comprises a flexible inhalation flap (or membrane), specifically a transparent plastic film adhesively attached along one edge to the inner surface of the inhalation valve assembly panel to cover the inhalation hole. Alternatively the inhalation valve flap may be hingeably connected to the inhalation valve assembly panel by a plurality of short, spaced hinge points.

The present invention provides an expandable/collapsible and in a preferred embodiment, disposable spacer for use with a MDI. The spacer is believed to possess one or more advantages or improvements over known expandable/collapsible and disposable spacers.

SUMMARY

According to a first aspect of the invention there is provided a spacer collapsible into a substantially flat configuration for storage and expandable into a spacer volume for use with a metered dose inhaler (MDI) wherein the spacer comprises:
  (a) a collapsible and expandable panel arrangement internally located within the spacer volume to divide the spacer volume into a MDI medicament delivery chamber and an inhalation/exhalation chamber when the spacer is in an expanded configuration;
  (b) a medicament delivery opening adapted to receive a MDI in a MDI medication delivery end of the MDI medicament delivery chamber;
  (c) an inhalation opening in a mouthpiece end of the inhalation/exhalation chamber;
  (d) an exhalation opening in the inhalation/exhalation chamber;
and further wherein the panel arrangement comprises an aperture off-set from the medicament delivery opening with the proviso that the aperture is not a valved aperture.

In one embodiment according to the first aspect the panel arrangement comprises at least two panels and one fold to form a zig-zag panel configuration wherein each panel has an exposed panel surface with respect to the medicament delivery chamber.

In another embodiment the panel arrangement comprises at least three panels and two folds to form a zig-zag panel configuration wherein each panel has an exposed panel surface with respect to the medicament delivery chamber.

In yet another embodiment the panel arrangement comprises at least four panels and three folds to form a zig-zag panel configuration wherein each panel has an exposed panel surface with respect to the medicament delivery chamber. In a further embodiment the panel arrangement comprises more than four panels and three folds to form a zig-zag panel configuration.

According to a second aspect of the invention there is provided a spacer collapsible into a substantially flat configuration for storage and expandable into a spacer volume for use with a metered dose inhaler (MDI) wherein the spacer comprises:
  (a) a collapsible and expandable panel arrangement internally located within the spacer volume to divide the spacer into a MDI medicament delivery chamber and an inhalation/exhalation chamber when the spacer is in an expanded configuration;
  (b) a medicament delivery opening adapted to receive a MDI in a MDI medication delivery end of the MDI medicament delivery chamber;
  (c) an inhalation opening in a mouthpiece end of the inhalation/exhalation chamber;
  (d) an exhalation opening in the inhalation/exhalation chamber;
and further wherein the panel arrangement comprises:
  (e) at least two panels and one fold to form a zig-zag panel configuration wherein each panel has an exposed panel surface with respect to the medicament delivery chamber; and
  (f) an aperture in one of the panels wherein the aperture is off-set from the medicament delivery opening;
with the proviso that the aperture is not a valved aperture.

In one embodiment the panel arrangement comprises at least three panels and two folds to form a zig-zag panel configuration wherein each panel has an exposed panel surface with respect to the medicament delivery chamber.

In another embodiment the panel arrangement comprises at least four panels and three folds to form a zig-zag panel configuration wherein each panel has an exposed panel surface with respect to the medicament delivery chamber. In a further embodiment the panel arrangement comprises more than four panels and three folds to form a zig-zag panel configuration.

In one embodiment according to the first and second aspects of the invention the spacer volume is formed by a top body panel joined to a bottom body panel along an edge to form the mouthpiece end wherein the remaining edges of the top body panel are each independently joined to a corresponding edge of the bottom body panel via a collapsible and expandable wall arrangement between them comprising:
  (i) two opposing side walls; and
  (ii) one wall distally located to the mouthpiece end to form the MDI medication delivery end;
and further wherein the internally located collapsible and expandable panel arrangement is joined to the top body panel and the bottom body panel such that when the spacer is in a collapsed configuration for storage the panel arrangement is in a collapsed configuration and when the spacer is in an expanded configuration for use the panel arrangement is in an expanded configuration.

According to a third aspect of the invention there is provided a spacer collapsible into a substantially flat configuration for storage and expandable into a spacer volume for use with a metered dose inhaler (MDI) wherein the spacer comprises:

(a) spacer volume formed by a top body panel joined to a bottom body panel along an edge to form the mouthpiece end wherein the remaining edges of the top panel are each independently joined to a corresponding edge of the bottom body panel via a collapsible and expandable wall arrangement between them comprising:
  (i) two opposing side walls; and
  (ii) one wall distally located to the mouthpiece end to form a MDI medication delivery end;
(b) a collapsible and expandable panel arrangement internally located within the spacer to divide the spacer volume into a MDI medicament delivery chamber and an inhalation/exhalation chamber when the spacer is in an expanded configuration wherein the panel arrangement is joined to the top body panel and the bottom body panel such that when the spacer is in a collapsed configuration for storage the panel arrangement is in a collapsed configuration and when the spacer is in an expanded configuration for use the panel arrangement is in an expanded configuration;
(c) a medicament delivery opening adapted to receive a MDI in the MDI medication delivery end of the MDI medicament delivery chamber of the spacer;
(d) an inhalation opening in the mouthpiece end of the inhalation/exhalation chamber of the spacer;
(e) an exhalation opening in the inhalation/exhalation chamber of the spacer;

and further wherein the panel arrangement comprises an aperture off-set from the medicament delivery opening with the proviso that the aperture is not a valved aperture.

In one embodiment according to the third aspect the panel arrangement comprises at least two panels and one fold to form a zig-zag panel configuration wherein each panel has an exposed panel surface with respect to the medicament delivery chamber.

In another embodiment the panel arrangement comprises at least three panels and two folds to form a zig-zag panel configuration wherein each panel has an exposed panel surface with respect to the medicament delivery chamber.

In yet another embodiment the panel arrangement comprises at least four panels and three folds to form a zig-zag panel configuration wherein each panel has an exposed panel surface with respect to the medicament delivery chamber. In a further embodiment the panel arrangement comprises more than four panels and three folds to form a zig-zag panel configuration.

According to a fourth aspect of the invention there is provided a spacer collapsible into a substantially flat configuration for storage and expandable into a spacer volume for use with a metered dose inhaler (MDI) wherein the spacer comprises:

(a) spacer formed by a top body panel joined to a bottom body panel along an edge to form the mouthpiece end wherein the remaining edges of the top body panel are each independently joined to a corresponding edge of the bottom body panel via a collapsible and expandable wall arrangement between them comprising:
  (i) two opposing side walls; and
  (ii) one wall distally located to the mouthpiece end to form a MDI medication delivery end;
(b) a collapsible and expandable panel arrangement internally located within the spacer volume to divide the spacer into a MDI medicament delivery chamber and an inhalation/exhalation chamber when the spacer is in an expanded configuration wherein the panel arrangement is joined to the top body panel and the bottom body panel such that when the spacer is in a collapsed configuration for storage the panel arrangement is in a collapsed configuration and when the spacer is in an expanded configuration for use the panel arrangement is in an expanded configuration;
(c) a medicament delivery opening adapted to receive a MDI in the MDI medication delivery end of the MDI medicament delivery chamber of the spacer;
(d) an inhalation opening in the mouthpiece end of the inhalation/exhalation chamber of the spacer;
(e) an exhalation opening in the inhalation/exhalation chamber of the spacer; and further wherein the panel arrangement comprises:
(f) at least two panels and one fold to form a zig-zag panel configuration wherein each panel has an exposed panel surface with respect to the medicament delivery chamber; and
(g) an aperture in one of the panels wherein the aperture is off-set from the medicament delivery opening;
with the proviso that the aperture is not a valved aperture.

In one embodiment the panel arrangement comprises at least three panels and two folds to form a zig-zag panel configuration wherein each panel has an exposed panel surface with respect to the medicament delivery chamber.

In another embodiment the panel arrangement comprises at least four panels and three folds to form a zig-zag panel configuration wherein each panel has an exposed panel surface with respect to the medicament delivery chamber. In a further embodiment the panel arrangement comprises more than four panels and three folds to form a zig-zag panel configuration.

It will be understood that use of the terms 'top', 'bottom' and 'side' with respect to the body and wall panels of the spacer are used herein as relative terms only and solely as a point of reference with respect to the orientation of the spacer as intended for normal operation.

DETAILED DESCRIPTION

Figure 1:
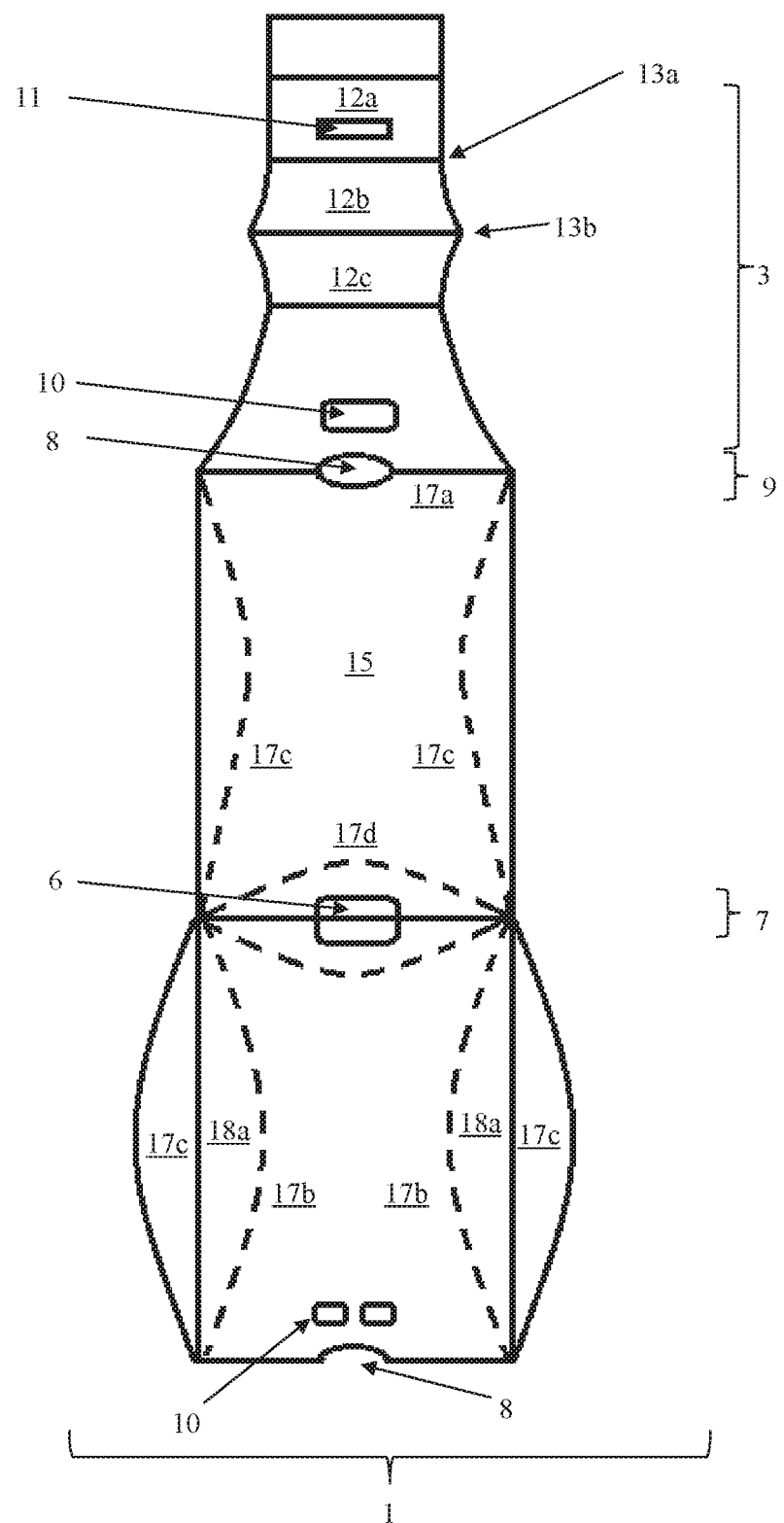
FIG. 1 shows a key line drawing for a single punched sheet for constructing a collapsible and expandable spacer in accordance with an embodiment of the invention.

The present invention provides a collapsible and expandable spacer for use with a metered dose inhaler (MDI). A disadvantage of known spacers, in particular collapsible/expandable and disposable spacers, such as the Lite Air® spacer (Thayer Medical Corporation, patent numbers U.S. Pat. Nos. 6,202,643, 6,550,473 and 6,679,252), is that they rely on a valve arrangement. However, valve arrangements require movable parts and may often be formed from two different types of material which require separate production and assembly thereby adding to the cost and complexity of the device. For example, the valve arrangement of the Lite Air® spacer has a valve flap which is made of plastic film and separately attached to the main spacer body which is made from a paper-based material. In addition, plastic films have the potential to build up static and attract medicament particles to their surface which may reduce the delivered dose or reduce the spacer's performance.

The present invention obviates the need to employ a valve arrangement while achieving similar or better performance in the delivery of a medicament from a MDI when compared to a disposable, collapsible/expandable spacer such as the Lite Air®. Without wishing to be bound by theory it is considered that the panel arrangement comprising an off-set aperture (i.e., out of alignment with the medicament delivery opening along the longitudinal axis of the spacer) obviates the need to employ a valve arrangement without substantially compromising the performance of the spacer.

Definitions

Unless otherwise herein defined, the following terms will be understood to have the general meanings which follow.

'Fold' or variations thereof such as 'foldable' will be understood to include fold lines.

'MDI' will be understood to mean a metered dose inhaler and includes pressurised metered dose inhalers, pMDI.

Embodiments

Embodiments of the invention will now be described with reference to the non-limiting examples which follow.

In one embodiment, two adjoining panels of the zig-zag panel configuration comprise a fold in a direction pointing towards the mouthpiece end wherein the fold is substantially in alignment with the medicament delivery opening along the longitudinal axis of the spacer.

In another embodiment, two adjoining panels of the zig-zag panel configuration comprise a fold in a direction pointing away from the mouthpiece end wherein the fold is substantially in alignment with the medicament delivery opening along the longitudinal axis of the spacer.

In one embodiment the aperture is located in a panel of the zig-zag panel configuration wherein the panel is adjacent to the top body panel or the bottom body panel of the spacer.

In one embodiment the aperture is located in a panel of the zig-zag panel configuration wherein the panel is adjacent to the top body panel of the spacer and the exhalation opening is located in the bottom body panel of the spacer.

In one embodiment the aperture is located in a panel of the zig-zag panel configuration wherein the panel is adjacent to the top body panel of the spacer and the exhalation opening is located in the top body panel of the spacer.

In one embodiment the aperture is located in a panel of the zig-zag panel configuration wherein the panel is adjacent to the bottom body panel of the spacer and the exhalation opening is located in the top body panel of the spacer.

In one embodiment the aperture is located in a panel of the zig-zag panel configuration wherein the panel is adjacent to the bottom body panel of the spacer and the exhalation opening is located in the bottom body panel of the spacer.

In one embodiment, the zig-zag panel configuration comprises two panels and one fold wherein each panel has an exposed panel surface with respect to the medicament delivery chamber.

In another embodiment, the zig-zag panel configuration comprises three panels and two folds wherein each panel has an exposed panel surface with respect to the medicament delivery chamber.

In yet another embodiment, the zig-zag panel configuration comprises four panels and three folds wherein each panel has an exposed panel surface with respect to the medicament delivery chamber.

In one embodiment the edge joining the top body panel to the bottom body panel to form the mouthpiece end comprising the inhalation opening is a folded edge. In another embodiment the top body panel is joined to the bottom body panel along an edge to form the mouthpiece end via a collapsible and expandable wall to form a collapsible and expandable mouthpiece end comprising the inhalation opening.

In one embodiment the spacer is formed from a disposable material. In one embodiment the spacer is formed from a single punched sheet of foldable material. Suitable materials may include, for example, paperboard, cardboard, plastics and polymers. In one embodiment the material is recyclable.

Figure 2:
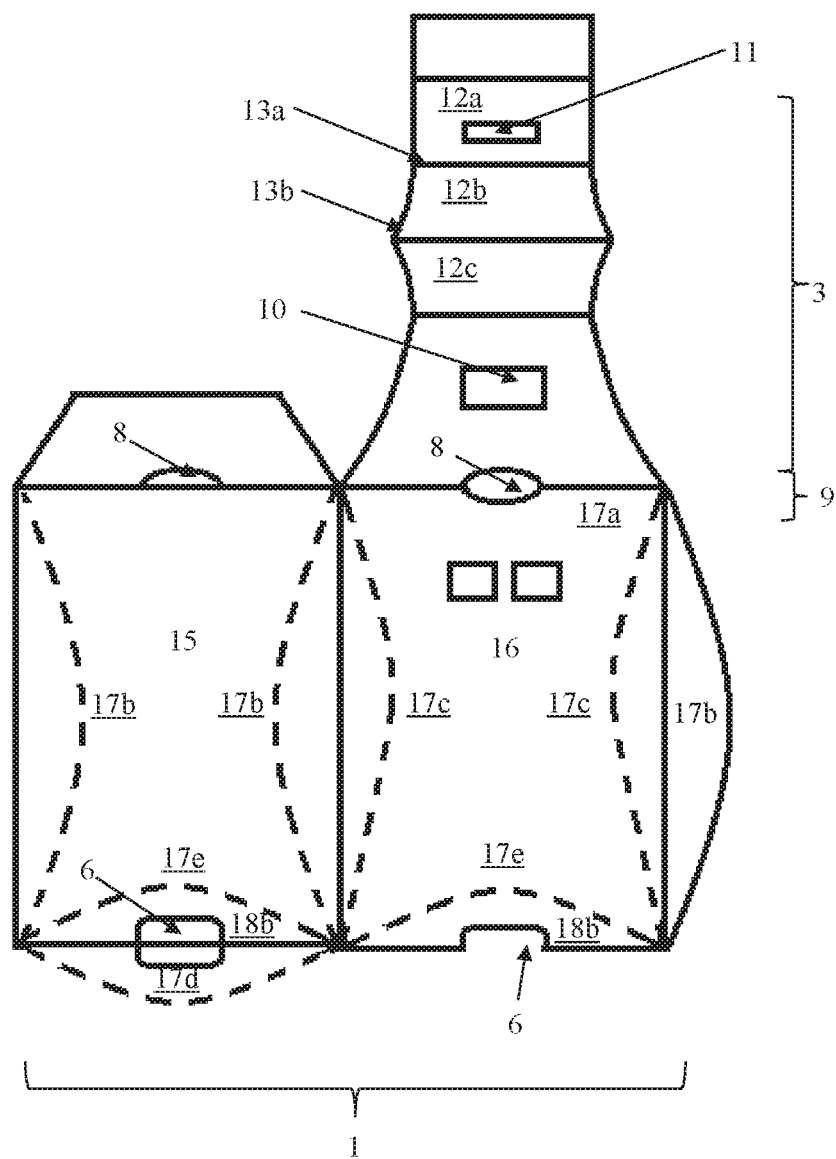
FIG. 2 shows an alternative version of key line drawing for a single punched sheet for constructing a collapsible and expandable spacer in accordance with an embodiment of the invention.
Figure 3:
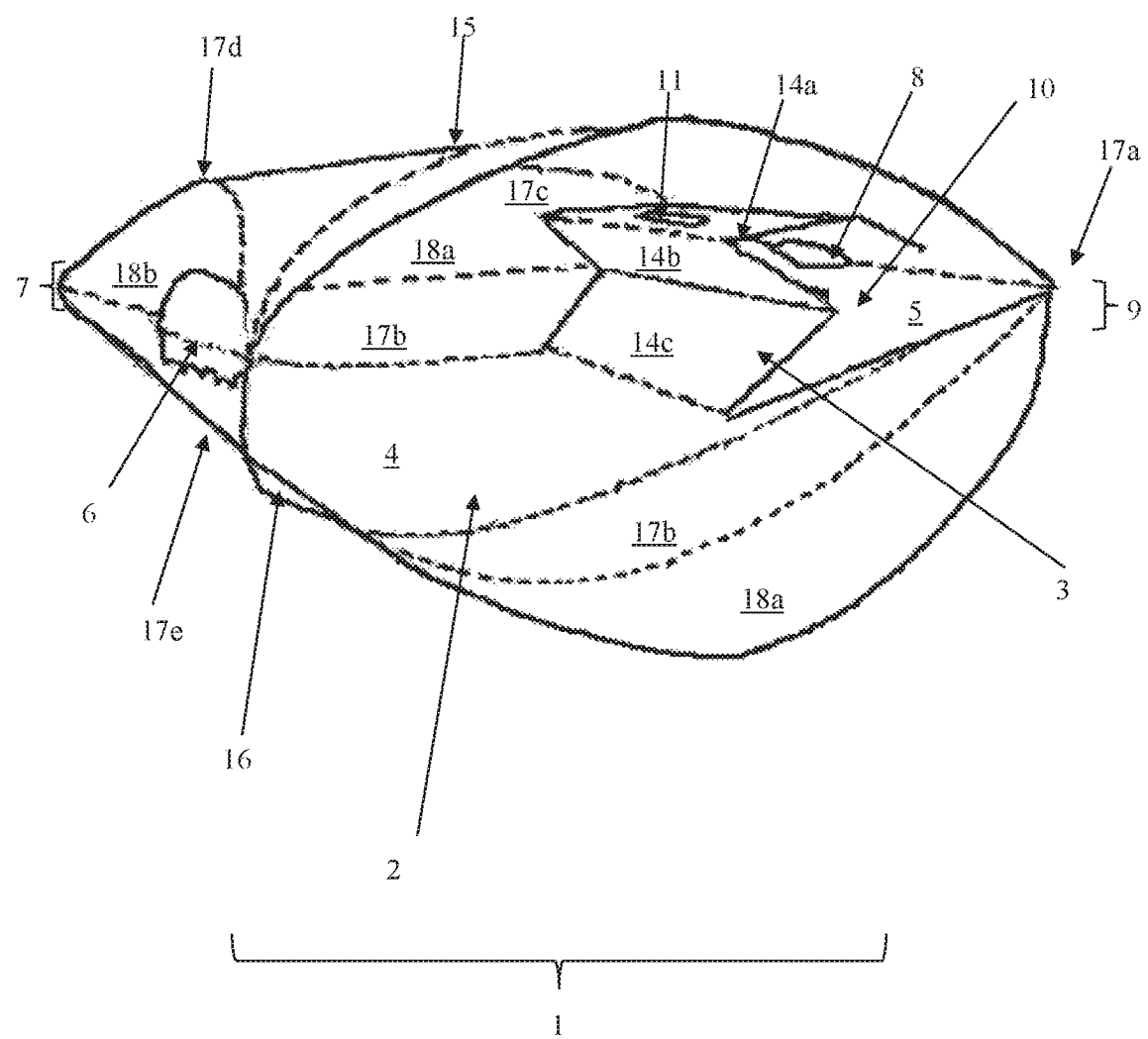
FIG. 3 shows a cut-away perspective view the spacer of FIG. 1 and FIG. 2 when assembled to illustrate the collapsible and expandable panel arrangement in an expanded configuration for use by a patient.

In one embodiment, the spacer is the spacer of FIG. 3. The spacer of FIG. 3 may be assembled from a single punched sheet, including as shown in FIG. 1 or FIG. 2. When required for use, the spacer (1) is expanded to create a spacer volume (2) which is divided by a collapsible and expandable panel arrangement (3) into a MDI medicament delivery chamber (4) and an inhalation/exhalation chamber (5). The spacer has a medicament delivery opening (6) in the medicament delivery end (7) of chamber (4) which is designed to fit and receive a MDI. This type of opening is sometimes referred to as a MDI boot adapter.

In use, a patient activates the MDI to deliver drug which travels through the spacer volume (2) to be inhaled by the patient through an inhalation opening (8) in the mouthpiece end (9) of chamber (5) and is subsequently exhaled out of chamber (5) via an exhalation opening (10). The drug that passes through the off-set aperture (11) is available for inhalation by the patient. The aperture is positioned in the zig-zag panel arrangement which is shown with three panels (12a, 12b, 12c) and two folds (13a, 13b), so that it is out of alignment with the medicament delivery (6) and inhalation (8) openings along the longitudinal axis of the spacer and hence main direction of drug delivery. The drug that does not pass through the off-set aperture (11) impacts the exposed panel surfaces (14a, 14b, 14c) where it may recirculate in chamber (4) and become available again to the patient upon the next inhalation.

The spacer (1) itself may be formed by a top body panel (15) which is joined to a bottom body panel (16) along one edge. To enable construction of the spacer from a single punched sheet, the mouthpiece end may be formed by a fold line between the top body panel and bottom body panel (17a). The collapsible and expandable panel arrangement (3) may then be folded up and attached, for example, by a suitable adhesive to the internal side of the top and bottom body panels. The remaining edges (e.g. 17b/17c and 17d/17e) are joined via a collapsible and expandable wall arrangement to form either one of two opposing side walls (e.g. 18a) or a wall with the boot adapter (18b).

EXAMPLE 1

A preliminary drug delivery performance test of an embodiment of the spacer according to the present invention (as shown in FIG. 3) was conducted as follows.

Equipment

Seven stage Next Generation Impactor (NGI) for pharmaceutical dry powder and metered dose inhalers (MDIs) with Micro-Office Collector (MOC): COPLEY Scientific Next Generation Pharmaceutical Impactor S/N NGI-0979

Pump: COPLEY Low Capacity Pump (LCP5)

Parameters

Flow rate (L/min): 30 L/min

Stages (D50 diameter, μm) where D50 represents the medium value of the particle size distribution: Throat (14.9); Stage 1 (11.7); Stage 2 (6.40); Stage 3 (3.99); Stage 4 (2.30); Stage 5 (1.36); Stage 6 (0.83); and Stage 7 (0.54).

Drug: Salbutamol sulfate
pMDI: Ventolin KN7365
Experiment

Selected drug delivery performance parameters of the spacer (as shown in FIG. 3) were tested using the pMDI and compared against the against the drug delivery performance of the pMDI alone and the pMDI in use with the Lite Air® spacer currently on the market, an essential feature of that spacer being its one-way valved aperture to control the flow of inhaled and exhaled air for drug delivery.

The drug deposited in the NGI was measured at each stage by HPLC.

The results are presented in Table 1 (n=1) and Table 2. Respirable stages are considered to be those from Stage 4 onwards. These preliminary results showed that the performance of the spacer when compared to use of the pMDI alone was comparable with regard to average respirable dose while greatly reducing the level of pharmaceutical deposited in the throat. Surprisingly, despite the absence of a valved aperture in the spacer to control the flow of inhaled and exhaled air these preliminary results also showed that the performance of the spacer was at least equivalent to the Lite Air® spacer (valved aperture) in all test categories according to Canadian standard Z264.1-02.

TABLE 1

Aerodynamic particle size distribution of drug delivered by pMDI alone, pMDI with spacer and pMDI with Lite Air® spacer

| Total Drug Mass Delivered at each Stage (μg) | pMDI | pMDI with spacer | pMDI with Lite Air® spacer |
|---|---|---|---|
| Throat | 362.57 | 29.32 | 6.85 |
| Stage 1 | 21.67 | 4.61 | 4.98 |
| Stage 2 | 16.29 | 6.09 | 5.75 |
| Stage 3 | 36.57 | 14.35 | 16.02 |
| Stage 4 | 93.97 | 64.96 | 70.89 |
| Stage 5 | 88.46 | 86.30 | 91.46 |
| Stage 6 | 26.90 | 27.13 | 29.85 |
| Stage 7 | 7.47 | 7.17 | 7.51 |
| MOC | 5.00 | 3.35 | 4.58 |
| NGI Final Filter | 17.51 | 13.86 | 16.94 |

TABLE 2

Comparative drug delivery performance parameters of pMDI alone, pMDI with spacer and pMDI with Lite Air® spacer for Total Delivered Dose (TDD)[1],[2]

| Device | TDD | FPD[3] (μg) ≤ 4.7 μm | % FPD ≤ 4.7 μm | MMAD[4] (μm) | GSD[5] |
|---|---|---|---|---|---|
| pMDI | 112.74 (0.20) | 39.38 (1.66) | 35.86 (1.46) | 2.58 (0.04) | 2.18 (0.12) |
| pMDI with spacer | 43.17 (1.10) | 32.26 (1.03) | 78.02 (0.44) | 2.09 (0.01) | 1.69 (0.01) |
| pMDI with Lite Air® spacer | 42.47 (0.55) | 35.19 (0.25) | 88.75 (0.68) | 2.09 (0.02) | 1.71 (0.01) |

[1]TDD = Total Delivered Dose inclusive of the NGI final filter noting the actual/theoretical dose is 100.00;
[2]Figures in brackets are standard error margin;
[3]FPD = Fine Particle Dose;
[4]MMAD = Mass Median Aerodynamic Diameter;
[5]GSD = Geometric Standard Deviation.

Throughout this specification and the claims which follow, unless the context requires otherwise, the word "comprise" and variations thereof such as "comprises" and "comprising", will be understood to include the inclusion of a stated integer or step or group of integers or steps but not the exclusion of any other integer or step or groups of integers or steps.

The reference in this specification to any prior publication, or information derived from it, or to any matter which is known, is not, and should not be taken as an acknowledgement or admission or any form of suggestion that the prior publication, or information derived from it, or known matter forms part of the common general knowledge in the field of endeavour to which this specification relates.

It will be understood to persons skilled in the art of the invention that modifications may be made without departing from the spirit and scope of the invention. The embodiments and/or examples as described herein are therefore to be considered as illustrative and not restrictive.

The invention claimed is:

1. A spacer collapsible into a substantially flat configuration for storage and expandable into a spacer volume for use with a metered dose inhaler (MDI) wherein the spacer comprises:
   (a) a collapsible and expandable panel arrangement internally located within the spacer volume to divide the spacer volume into a MDI medicament delivery chamber and an inhalation/exhalation chamber when the spacer is in an expanded configuration;
   (b) a medicament delivery opening adapted to receive a MDI in a MDI medication delivery end of the MDI medicament delivery chamber;
   (c) an inhalation opening in a mouthpiece end of the inhalation/exhalation chamber;
   (d) an exhalation opening in the inhalation/exhalation chamber;
   and further wherein the panel arrangement comprises an aperture off-set from the medicament delivery opening, and wherein the aperture is not a valved aperture.

2. A spacer according to claim 1, wherein the panel arrangement comprises at least two panels and one fold to form a zig-zag panel configuration wherein each panel has an exposed panel surface with respect to the MDI medicament delivery chamber.

3. The spacer according to claim 2, wherein the panel arrangement comprises at least three panels and two folds to form a zig-zag panel configuration and wherein each panel has an exposed panel surface with respect to the MDI medicament delivery chamber.

4. The spacer according to claim 3, wherein the panel arrangement comprises at least four panels and three folds to form a zig-zag panel configuration wherein each panel has an exposed panel surface with respect to the MDI medicament delivery chamber.

5. The spacer according to claim 4, wherein the panel arrangement comprises more than four panels and three folds to form a zig-zag panel configuration.

6. The spacer according to claim 2, wherein two adjoining panels of the zig-zag panel configuration comprise a fold in a direction pointing towards the mouthpiece end wherein the fold is substantially in alignment with the medicament delivery opening along a longitudinal axis of the spacer.

7. The spacer according to claim 2, wherein two adjoining panels of the zig-zag panel configuration comprise a fold in a direction pointing away from the mouthpiece end wherein the fold is substantially in alignment with the medicament delivery opening along a longitudinal axis of the spacer.

8. The spacer according to claim 2, wherein the spacer volume is formed by a top body panel joined to a bottom body panel along an edge to form the mouthpiece end, wherein the aperture is located in a panel of the zig-zag panel configuration, and wherein the panel is adjacent to the top body panel or the bottom body panel of the spacer.

9. The spacer according to claim 2, wherein the spacer volume is formed by a top body panel joined to a bottom body panel along an edge to form the mouthpiece end, and wherein the aperture is located in a panel of the zig-zag panel configuration wherein the panel is adjacent to the top body panel of the spacer and the exhalation opening is located in the bottom body panel of the spacer.

10. The spacer according to claim 2, wherein the spacer volume is formed by a top body panel joined to a bottom body panel along an edge to form the mouthpiece end, wherein the aperture is located in a panel of the zig-zag panel configuration, and wherein the panel is adjacent to the top body panel of the spacer and the exhalation opening is located in the top body panel of the spacer.

11. The spacer according to claim 2, wherein the spacer volume is formed by a top body panel joined to a bottom body panel along an edge to form the mouthpiece end, wherein the aperture is located in a panel of the zig-zag panel configuration, and wherein the panel is adjacent to the bottom body panel of the spacer and the exhalation opening is located in the top body panel of the spacer.

12. The spacer according to claim 2, wherein the spacer volume is formed by a top body panel joined to a bottom body panel along an edge to form the mouthpiece end, wherein the aperture is located in a panel of the zig-zag panel configuration, and wherein the panel is adjacent to the bottom body panel of the spacer and the exhalation opening is located in the bottom body panel of the spacer.

13. The spacer according to claim 1, wherein the spacer volume is formed by a top body panel joined to a bottom body panel along an edge to form the mouthpiece end wherein the remaining edges of the top body panel are each independently joined to a corresponding edge of the bottom body panel via a collapsible and expandable wall arrangement between them comprising:
 (i) two opposing side walls; and
 (ii) one wall distally located to the mouthpiece end to form the MDI medication delivery end;
and further wherein the internally located collapsible and expandable panel arrangement is joined to the top body panel and the bottom body panel such that when the spacer is in a collapsed configuration for storage the panel arrangement is in a collapsed configuration and when the spacer is in an expanded configuration for use the panel arrangement is in an expanded configuration.

14. The spacer according to claim 13, wherein the edge joining the top body panel to the bottom body panel to form the mouthpiece end comprising the inhalation opening is a folded edge.

15. The spacer according to claim 13, wherein the top body panel is joined to the bottom body panel along an edge to form the mouthpiece end via a collapsible and expandable wall to form a collapsible and expandable mouthpiece end comprising the inhalation opening.

16. The spacer according to claim 1, wherein the spacer is formed from a disposable material.

17. The spacer according to claim 1, wherein the spacer is formed from a single punched sheet of foldable material.

* * * * *